US009615571B2

(12) United States Patent
Olson et al.

(10) Patent No.: US 9,615,571 B2
(45) Date of Patent: Apr. 11, 2017

(54) ORGAN/TISSUE DISSECTION BASIN SYSTEM

(71) Applicants: Leslie Charles Olson, Issaquah, WA (US); Andrew Stephen Ouderkirk Malcolm, Seattle, WA (US)

(72) Inventors: Leslie Charles Olson, Issaquah, WA (US); Andrew Stephen Ouderkirk Malcolm, Seattle, WA (US)

( * ) Notice: Subject to any disclaimer, the term of this patent is extended or adjusted under 35 U.S.C. 154(b) by 186 days.

(21) Appl. No.: 14/284,302

(22) Filed: May 21, 2014

(65) Prior Publication Data
US 2014/0272922 A1   Sep. 18, 2014

Related U.S. Application Data

(62) Division of application No. 13/726,103, filed on Dec. 22, 2012, now abandoned.

(60) Provisional application No. 61/594,582, filed on Feb. 3, 2012.

(51) Int. Cl.
| | |
|---|---|
| *A01N 1/00* | (2006.01) |
| *C12M 1/00* | (2006.01) |
| *C12M 3/00* | (2006.01) |
| *A01N 1/02* | (2006.01) |

(52) U.S. Cl.
CPC .................................. *A01N 1/0263* (2013.01)

(58) Field of Classification Search
CPC ..... C12M 23/04; C12M 21/08; A01N 1/0242; A01N 1/0236; A01N 1/02
See application file for complete search history.

(56) References Cited

U.S. PATENT DOCUMENTS

| | | | | |
|---|---|---|---|---|
| 4,953,540 A | * | 9/1990 | Ray .................... | A61B 17/0293 600/233 |
| 4,971,038 A | * | 11/1990 | Farley .................... | A61B 17/02 24/525 |
| 5,272,083 A | * | 12/1993 | Butz ...................... | C12M 23/00 422/552 |
| 5,803,903 A | * | 9/1998 | Athas ................. | A61B 17/0293 600/201 |
| 6,834,837 B2 | * | 12/2004 | Schilt ..................... | A61B 90/50 248/276.1 |

FOREIGN PATENT DOCUMENTS

WO   WO 97/49370 A1 * 12/1997

* cited by examiner

*Primary Examiner* — Nathan Bowers
(74) *Attorney, Agent, or Firm* — Plager Schack LLP

(57) ABSTRACT

A basin system is provided comprising a basin, a tissue supporting plate, a platform ring and a suspension rod, the basin system configured to permit a single clinician to effectively and accurately perform the dissection with minimal movement of the resected tissue within the basin system, wherein the platform ring and the suspension rod each comprise a plurality of grooves, permitting a clinician to secure resected tissue within the basin system and tie it down in three dimensions.

3 Claims, 3 Drawing Sheets

ORGAN/TISSUE DISSECTION BASIN SYSTEM

RELATED APPLICATION

This application is a divisional application of U.S. non-provisional patent application Ser. No. 13/726,103 filed on Dec. 22, 2012, which in turn claims priority to provisional patent application U.S. Ser. No. 61/594,582 filed on Feb. 3, 2012, the entire contents of both applications are herein incorporated by reference.

BACKGROUND

The embodiments herein relate generally to a system for stabilizing resected tissue, such as organs, by clinicians while preparing the tissue for transplant, and more specifically to a sterile basin for securing the resected tissue in three dimensions to more effectively permit a single clinician to prepare the tissue without the aid of a second clinician.

Historically, donated tissue, including organs, are dissected in a basin filled with preservation solution. The organ partially floats in the solution, which, not surprisingly, causes the organ to move while surgical dissection is preformed prior to transplantation. That tendency toward movement often requires a second clinician to participate to stabilize the organ while the first clinician performs the dissection of the surrounding undesired tissue.

While prior efforts have been made to stabilize the tissue and/or organ within the basin, none seem to fully relieve the need for a second clinician to permit a single clinician to accurately and effectively prepare the tissue for transplantation. Or, more importantly, even where a single clinician performs the dissection, the risk of movement reduces the speed of dissection and increases the risk of organ or vessel damage. Embodiments of the invention herein overcome at least this problem.

SUMMARY

In some embodiments of the present invention, a molded plate is employed to constrain the tissue, including organs, and permit a clinician to tack sutures with a surgical clamp to further demobilize the organ using a plurality of grooves in discrete ring and at least one of a plurality of grooves in an elevated extension. Such an arrangement permits the clinician to tack the organs vessels in a three dimensional state.

In one set of embodiments, a system is provided for the stabilized dissection of resected tissue, including organs, where the system is configured to stabilize the resected tissue so that a single clinician may employ the system to effectively and accurately perform the dissection with minimal movement of the resected tissue. The system may comprise a basin serving as a system base upon which dissection may take place, where the basin comprise a generally annular rim configuration; a tissue supporting plate configured in shape and size to accommodate in a semi-confined manner one or more particular categories of resected tissue, including organs, where the plate is further configured to securely fit within the basin in a stable manner during use; a platform ring having a generally annular configuration, where the platform ring comprising a generally flat flanged portion and a generally cylindrical collar portion, and the collar portion is configured to fit within the interior of the basin rim while the flanged portion is configured to rest upon the basin rim and extend radially outwardly, where the platform ring further comprises a plurality of grooves spaced radially about the outer profile of the platform ring flange.

The system may further comprises a suspension rod configured to be secured within the system so that at least a first portion of the suspension rod may be positioned so as to extend generally horizontally above and across the top of the platform ring when the system is in use, where the suspension rod comprises a plurality of grooves within the first portion, and the suspension rod further comprising a second portion for mounting the suspension rod within the system in a secure yet adjustable manner. With such an arrangement, the suspension rod may be securely adjusted for static positioning in one of a number of positions defined by both a height of the first portion above the platform ring and an angular position relative to the center of the tissue supporting plate such that, when in use, a clinician may orient both the platform ring and the first portion of the suspension rod relative to the tissue supporting plate and, using sutures securely applied to the tissue and to the grooves on the platform ring and at least one groove on the first portion of the suspension rod, secure the tissue in a stable minimally-movable position to permit accurate and controlled dissection.

In other embodiments, the platform ring may further comprise means for adjustably securing the platform ring to the basin. Moreover, the system may further comprise a second basin configured to hold therewithin the first basin.

In one application, a method is providing of using a basin system such as the example embodiment described above, and setting with a basin a tissue supporting plate; filling the basin with iced saline solution; floating within the iced saline solution a bag filled with resected tissue and preserving fluid; opening up the bag and draping the edges of the bag over the upper annular rim of the basin; placing the platform ring of the basin system on top of the draped edges and the annular rim of the basin; adjusting the suspension rod both in height and rotational position relative to the tissue supporting plate; securing a portion of the resected tissue within the basin system with a plurality of sutures so that such plurality of sutures has a free end; and securing each free end within at least two grooves of the platform ring and at least one groove of the suspension rod, thereby securing the resected tissue in a confined and secured manner sufficient to permit the clinician to perform more accurate and effective dissection. In an alternative application, the filling of the basin may comprise placing a bag of iced saline solution within the basin over the tissue supporting plate, opening up the bag, and draping the edges of the bag over the annual upper rim of the basin.

BRIEF DESCRIPTION OF THE FIGURES

The detailed description of some embodiments of the invention will be as described below with reference to the accompanying Figures, wherein like numerals represent corresponding parts of the Figures.

DETAILED DESCRIPTION OF CERTAIN EMBODIMENTS

Figure 1:
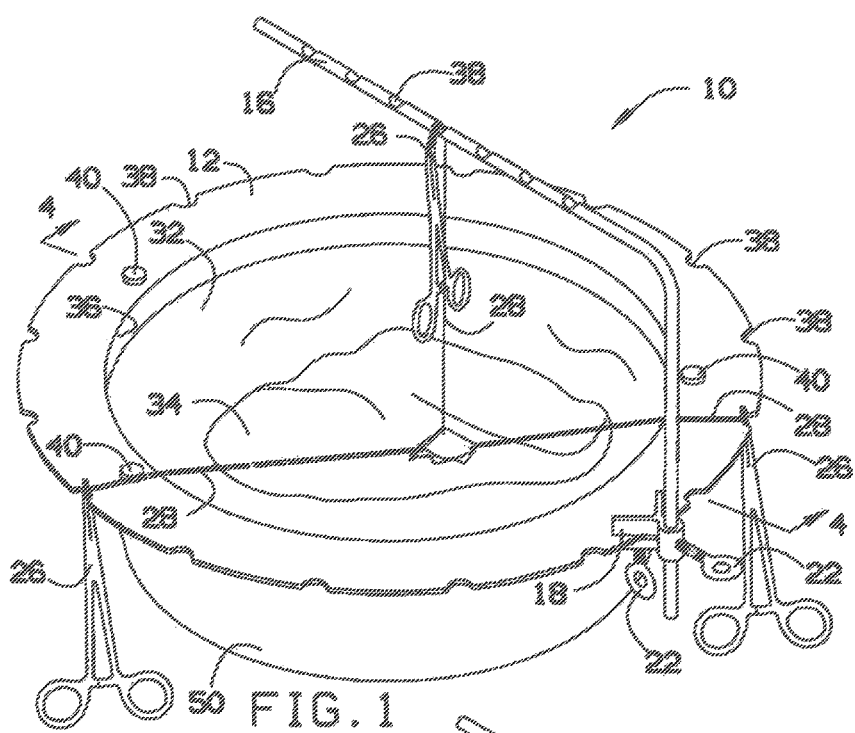
FIG. 1 is a perspective view of one embodiment of the present invention shown in use.

In embodiments of the present invention, a system is provided to permit controlled and accurate dissection of resected tissue whereby the system is configured so that the resected tissue may be secured in three dimensions, such as one example of an embodiment in use shown in FIG. 1, to be described in greater detail below.

Figure 2:
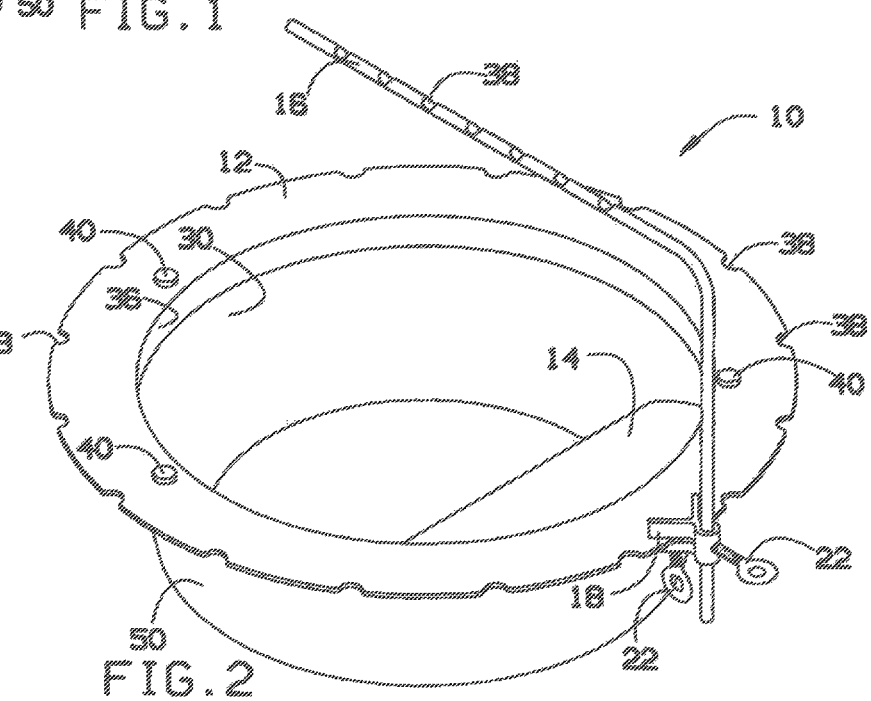
FIG. 2 is a perspective view of the embodiment of FIG. 1.
Figure 3:
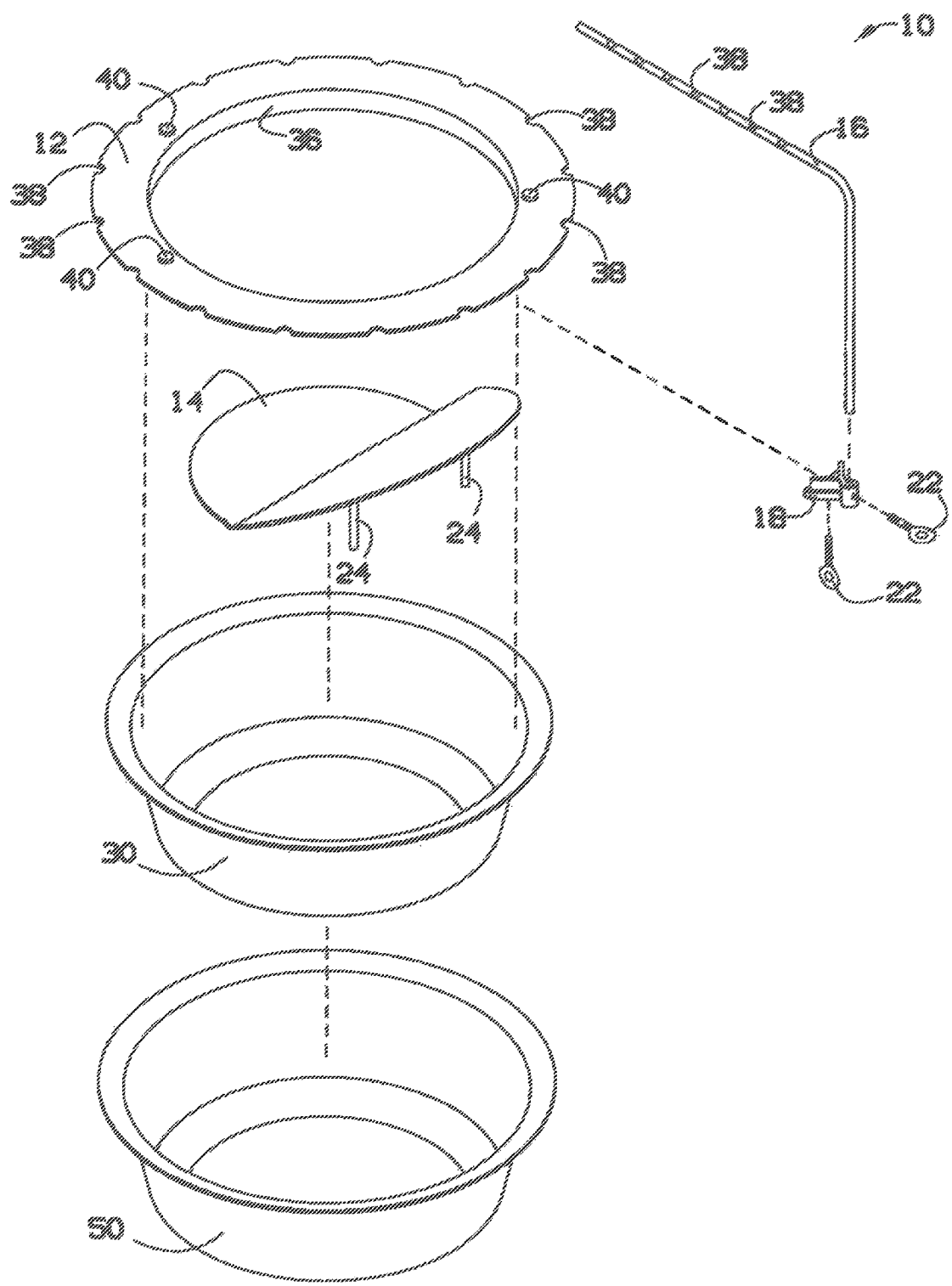
FIG. 3 is a perspective exploded view of components of the embodiment of FIG. 1.

Referring to FIGS. 2 and 3, one embodiment of the present invention may be described with specificity. A dissection system 10 comprises a platform ring 12, a tissue supporting plate 14, and a suspension rod 16 securable, in this example embodiment, to the platform ring 12 with an adjustable bracket 18 comprising one or more position adjustment means, such as thumb screws 22, although other fastening means may be employed. In one embodiment, the tissue supporting plate 14 is configured to rest securely upon one or more legs 24 within a first basin 30 having a generally annular upper rim upon which the platform ring 12 may rest.

In one embodiment, the suspension rod 16 comprises a first portion that is generally horizontal (when the rod 16 is secured within the system) and a second portion that is generally vertical (when the rod 16 is secured within the system). Such an arrangement permits the first portion of the suspension rod 16 to be suspended above the tissue supporting plate 14 and, thus, above whatever tissue may be confined within the basin 30 on the supporting plate 14. Of course, it should be appreciated that other means of securing the suspension rod 16 within the system 10 may be employed, including means for securing the suspension rod to the first basin 30 itself or a combination of the first basin 30 and the platform ring 12. In any manner, the means for secure adjustment, including the adjustable bracket 18, should permit adjustment of the suspension rod 16 both in height above the platform ring 12 and rotationally (i.e., in a swivelable manner) across the top of the tissue supporting plate 14.

In one embodiment, the platform ring 12 comprises a generally cylindrical collar 36 extending downwardly and configured preferably to fit securely within the upper rim of the basin 30. Preferably, the collar is configured so that, if the tissue supporting plate 14 is placed within the basin first, and then the platform ring 12 placed upon the upper rim of the basin 30, the collar 36 abuts the uppermost portion of the tissue supporting plate 14 to help restrain its inadvertent movement, as shown by example in FIG. 4.

The platform ring 12 importantly comprises means for stabilizing any tissue residing on the tissue supporting plate 14 within the basin 30. In one embodiment, such means comprises a plurality of radially-spaced grooves 38 within a generally flat flange portion of the platform ring 12 surrounding the collar 36. If desired, means may be provided for securing the platform ring 12 to the basin 30, including mechanical fasteners (not shown), or the platform ring 12 may be constructed of sufficiently heavy material to rest securely upon the upper rim of the basin 30. In one embodiment, the fasteners are radially positioned strategically to permit the clinician to orient the platform ring 12 relative to the tissue supporting plate 14 and basin 30 as needed. In that regard, if desired, position knobs 40 may be employed on the platform ring 12 to function essentially as guides for a cover (not shown), where the diameter represented by the plurality of knobs 40 is just slightly smaller than the diameter of the cover so that the cover may be placed on top of the basin system and remain stable during movement of the basin system. In other words, the knobs 40 would prevent the cover from sliding laterally off as the basin system is moved on the table. If so desired, the knobs 40 could also serve to indicate relative orientation of the platform ring 12 relative to the tissue support plate 14 and/or basin 30.

As with the flange portion of the platform ring 12, which has a plurality of grooves 38, the first portion of the suspension rod 16 also preferably comprises means for restraining resected tissue, including grooves 38 that may or may not be of the same configuration as the grooves 38 of the platform ring 12. Indeed, it is contemplated that the means for restrain provided in the platform ring and the first portion of the suspension rod may be one or more of numerous possible configurations that permit a clinician to tack a resected tissue within the basin 30 in a stable and secure manner for controlled dissection. Grooves are but one of the many configurations.

Providing for a plurality of grooves enhances the flexibility of the clinician to tack the resected tissue on the tissue supporting plate on one of a number of possible orientations to maximize the convenience of dissection of undesired peripheral portions of the resected tissue. For example, referring to FIG. 1, it may be appreciated that using sutures 28 and clamps 26, a clinician may affix the resected tissue residing (when in use) in the basin 30 at a desired location, and then in three directions (and thereby three dimensions) tie down (or tack) the resected tissue in a stable and essentially immovable manner to permit a single clinician to dissect portions of the resected tissue as desired.

Adjustability in the manner and orientation in how the resected tissue is tied down is provided in the adjustability of the rotational position of the platform ring 12 relative to the tissue support plate 14, the height and rotational position of the suspension rod 16 relative to the tissue support plate 14, and the selection of the three or more grooves in the platform ring 12 and suspension rod 16 upon which the sutures may be secured vis-à-vis securing means, such as the clamps 26. With each end of a suture extending from the resected tissue secured via a clamp 26, the clinician may in real-time readjust the 3-dimensional securement of the resected tissue simply by moving any one of the sutures to a different groove 38 or raising and/or swiveling the suspension rod 16.

As one of ordinary skill in the art may appreciate, the configuration of the tissue supporting plate 14 is preferably configured to help confine the resected tissue within the basin 30, and may be configured in one of many different manners to conform to specific designated tissues, such a particular organs (liver, kidneys, heart, pancreas, lungs, etc.) or lumenal tracts (e.g., intestines, vasculature, etc.). For example, one embodiment of a tissue supporting plate may be configured in size and shape to confine a liver, while another may be configured in size and shape to confine a kidney or entire renal system. In one embodiment, such as that shown in FIGS. 2 and 3, the tissue supporting plate 14 comprises a first portion comprising a generally flat configuration and a second portion angled with respect to the first portion to assist in confining the resected tissue to the first portion, with the first portion preferably resting within the base of the basin 30 and the second portion similarly preferably resting within the base of the basin 30 but upon the one or more legs 24. Or in the case of dissection of a resected bi-lobed lung, the angled second portion of the tissue supporting plate may serve to support the smaller lobe while the larger lobe rests on the first portion. In alternative embodiments, the legs may be adjustable and the first and second portions of the tissue supporting plate hinged so as to permit real-time adjustment of the angle of the second portion relative to the first portion to adjust confinement of the resected tissue or to accommodate a different size of tissue than was expected.

Figure 4:
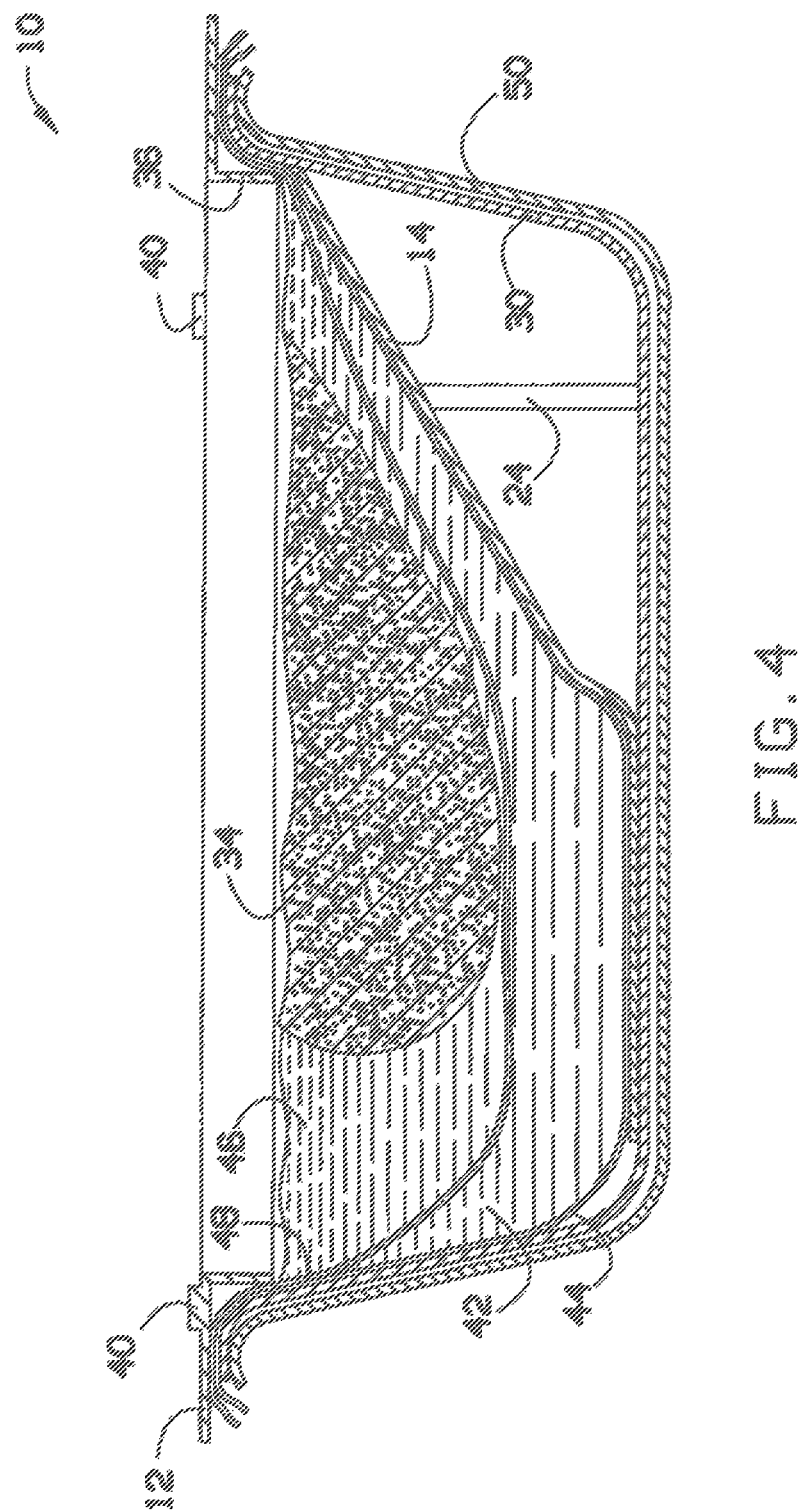
FIG. 4 is cross-sectional elevation view of the embodiment of FIG. 1 in use.

Referring to FIG. 4, use of one embodiment of the inventive system may be described in more detail. There it can be appreciated that a resected tissue 34 is typically secured with preserving fluid 46 within a first durable yet pliant intestinal bag 48. In one application, after placement of the tissue supporting plate 14 within basin 30, a second intestinal bag 44, for example, may be filled with iced saline solution 42 and opened up to secure the edges of the bag 44 over the upper rim of the basin 30. The first intestinal bag 48 contained the resected tissue 34 may be placed within the exposed iced saline solution 42, which the first bag 48 opened up so that its edges also drape over the upper rim of the basin 30. Then, preferably, the platform ring 12 is then placed over the bag edges and the upper basin rim to essentially lock the bags in place and to maintain the tissue supporting plate is a stable unmovable position. The suspension rod 16 may then be secured within the system 10 in a desired position. This arrangement alone is an improvement in confining the resected tissue. However, as described above, further confinement and securement is achieved by suturing the resected tissue and placing the ends of at least three sutures as described above in association with FIG. 1. The submerged organ now is presented with a stable platform for safer 'back table' dissection.

In one embodiment, the platform ring 12, the tissue supporting plate 14 and the basin 30 are constructed of stainless steel of sufficient thickness and shape to achieve the desired functionality alluded to herein. Other materials may be employed, of course, if so desired.

Indeed, other configurations are contemplated, as the embodiments described herein are by example only. For example, a second basin 50 may be employed to add an insulating layer surrounding the first basin 30. Insulation may by provided by at least one of two ways: by configuring the outer basin 50 such that it leaves an air gap between the interior surface of the outer basin 50 and the outer surface of the inner basin 30, and/or by manufacturing the outer basin out of material that has low heat transfer coefficient. FIG. 4 shows a relatively small air gap, but the air gap may be much larger depending upon the time expected for dissection of the tissue with the desire to keep it sufficiently chilled.

Preferably, the outer basin 50 is also configured with a low center of gravity or is configured (such as with a large diameter base) such that is may resist or diminish the risk of tipping if the clinicians inadvertently leans too hard on one side of the platform ring while working The outer basin may also be configured so as to assist in resisting movement of an otherwise smooth stainless steel basin 30 relative to the table upon which it rests during back table dissection. Preferably, such a second basin 50 is constructed of plastic or other material having a higher coefficient of friction than the stainless steel basin 30. It is also contemplated that the first basin need not be generally circular in geometry, but may comprise other shapes and sizes chosen to effectively secure within resected tissue for dissection, where in such embodiments, the tissue supporting plate and the platform ring is correspondingly configured to nest together as exemplified in a more circular embodiment shown in FIG. 4. In yet other embodiments, a plurality of suspension rods are employed to further enhance the multi-dimensional securement of the resected tissue in a number of opposing directions.

Given the possible variations on the embodiments contemplated herein, the scope of the invention is therefore reflected by the breadth of the claims below rather than limited by the embodiments described above.

What is claimed is:

1. A system for the stabilized dissection of resected tissue, including organs, the system configured to stabilize the resected tissue so that a single clinician may employ the system to effectively and accurately perform the dissection with minimal movement of the resected tissue, the system comprising:

a basin serving as a system based upon which dissection may take place; the basin comprising a generally annular rim configuration;

a tissue supporting plate having a lower portion immediately against a bottom of the basin; wherein the lower portion transitions upward toward the generally annular rim; wherein the upward transitioning portion is supported against the basin with at least one leg;

a platform ring having a generally annular configuration, the platform ring comprising a generally flat flanged portion and a generally cylindrical collar portion, the collar portion configured to fit within the interior of the basin rim while the flanged portion is configured to rest upon the basin rim and extend radially outwardly, the platform ring further comprising a plurality of grooves spaced radially about the outer profile of the platform ring flange; and a suspension rod attached to the platform ring with an adjustable bracket; so that at least a first portion of the suspension rod may be positioned so as to extend generally horizontally above and across the top of the platform ring when the system is in use, the suspension rod comprising a plurality of grooves within the first portion, the suspension rod further comprising a second portion for mounting the suspension rod within the adjustable bracket, whereby the suspension rod may be securely adjusted for static positioning in one of a number of positions defined by both a height of the first portion above the platform ring and an angular position relative to the center of the tissue supporting plate;

wherein, when in use, a clinician may orient both the platform ring and the first portion of the suspension rod relative to the tissue supporting plate and, using sutures securely applied to the tissue and to the grooves on the platform ring and at least one groove on the first portion of the suspension rod, secure the tissue in a stable minimally-movable position to permit accurate and controlled dissection.

2. The system of claim 1, wherein a plurality of knobs attached to the platform ring and configured to indicate relative orientation of the platform ring.

3. The system of claim 1, wherein the system further comprises a second basin configured to hold therewithin the first basin, wherein the second basin is configured to provide a layer of insulation surrounding the first basin.

* * * * *